(12) United States Patent
Kyei-Baffour et al.

(10) Patent No.: US 10,449,174 B2
(45) Date of Patent: Oct. 22, 2019

(54) ARYL ISONITRILE COMPOUNDS AS A NEW CLASS OF POTENT, BROAD-SPECTRUM ANTIFUNGAL COMPOUNDS

(71) Applicant: Purdue Research Foundation, West Lafayette, IN (US)

(72) Inventors: Kwaku Kyei-Baffour, West Lafayette, IN (US); Mohamed Seleem, West Lafayette, IN (US); Mingji Dai, West Lafayette, IN (US); Haroon Taj Mohammad, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 249 days.

(21) Appl. No.: 15/456,950

(22) Filed: Mar. 13, 2017

(65) Prior Publication Data

US 2017/0181997 A1    Jun. 29, 2017

Related U.S. Application Data

(63) Continuation-in-part of application No. 15/090,619, filed on Apr. 4, 2016.

(60) Provisional application No. 62/143,031, filed on Apr. 4, 2015.

(51) Int. Cl.
| | |
|---|---|
| *A61K 31/277* | (2006.01) |
| *A61K 31/4402* | (2006.01) |
| *A61K 31/4406* | (2006.01) |
| *A61K 31/4409* | (2006.01) |
| *C07D 213/38* | (2006.01) |
| *C07C 291/10* | (2006.01) |

(52) U.S. Cl.
CPC ........ *A61K 31/277* (2013.01); *A61K 31/4402* (2013.01); *A61K 31/4406* (2013.01); *A61K 31/4409* (2013.01); *C07D 213/38* (2013.01); *C07C 291/10* (2013.01); *C07C 2601/14* (2017.05)

(58) Field of Classification Search
CPC .............. A61K 31/277; A61K 31/4402; A61K 31/4406; A61K 31/4409; C07D 213/38; C07C 2601/14; C07C 291/10
See application file for complete search history.

(56) References Cited

U.S. PATENT DOCUMENTS

2007/0292545 A1    12/2007 Monte et al.

FOREIGN PATENT DOCUMENTS

WO    WO 99/13714    *    9/1998

OTHER PUBLICATIONS

Kumar et al. IJPSR, 2012, vol. 3(6): 1790-1794.*
Tokuyama et al. Synlett, 2001, No. 9, 1403-1406.*
Kabir, et al., New classes of Gram-Positive selective antibacterials: Inhibitors of MRSA and surrogates of the musative agents of anthrax and the tuberculosis, Bioorganic and Medicinal Chemistry Letters,2008, 18, 5745-5749.
Nitta et al., Antibacterial activity of extracts prepared from tropical or subtropical plants on Methicillin-resistant *Staphylococcus aureus*, Journal of Health Science, 48(3), 273-276.

* cited by examiner

*Primary Examiner* — Kara R McMillian
(74) *Attorney, Agent, or Firm* — Purdue Research Foundation; Zhigang Rao

(57) ABSTRACT

Invasive fungal infections present a formidable global public health challenge due to the limited number of approved antifungal agents and the emergence of resistance to the frontline treatment options, such as fluconazole. Three fungal pathogens of significant concern are *Candida*, *Cryptococcus*, and *Aspergillus* given their propensity to cause opportunistic infections in immunocompromised individuals. This disclosure provides a set of aryl isonitrile compounds that possess broad-spectrum antifungal activity primarily against species of *Candida* and *Cryptococcus*. The most potent derivatives are capable of inhibiting growth of these key pathogens at concentrations as low as 0.5 µM. Remarkably, the most active compounds exhibit an excellent safety profile and are non-toxic to mammalian cells even at concentrations up to 256 µM.

6 Claims, 7 Drawing Sheets

Table 1.

| Compound /Drug Name | Candida albicans | |
|---|---|---|
| | MIC | MFC |
| 1 | 4 | 32 |
| 2 | 2 | >64 |
| 3 | 2 | >64 |
| 4 | 8 | 64 |
| 5 | 64 | N.D.[1] |
| 6 | >64 | >64 |
| 7 | 2 | >64 |
| 8 | 32 | N.D. |
| 9 | 16 | N.D. |
| 10 | 1 | >64 |
| 11 | 2 | >64 |
| 12 | 8 | 64 |
| 13 | 8 | 64 |
| 14 | >64 | >64 |
| 15 | 16 | N.D. |
| 16 | 4 | >64 |
| 17 | >64 | >64 |
| 18 | 8 | >64 |
| 19 | 0.5 | >64 |
| 20 | 2 | 16 |
| 21 | 4 | >64 |
| 22 | 1 | 16 |
| 23 | 1 | 32 |
| 24 | 4 | 4 |
| 25 | 0.5 | 64 |
| 26 | 2 | 2 |
| 27 | 4 | 4 |
| 28 | 2 | 16 |
| 29 | 2 | 16 |
| 30 | 1 | 1 |
| 31 | 64 | N.D. |
| 32 | 0.5 | 64 |
| 33 | >64 | >64 |
| 34 | >64 | >64 |
| Fluconazole | 0.5 | >64 |

FIGURE 5

Table 2.

| Strain Name | Compound/Drug Name | | | | | | |
|---|---|---|---|---|---|---|---|
| | 2 | 22 | 23 | 25 | 26 | 32 | Fluconazole |
| *Candida albicans* ATCC 29351 | 1 | 1 | 2 | 1 | ≤0.5 | ≤0.5 | ≤0.5 |
| *Candida albicans* ATCC 27365 | 1 | 1 | 2 | 2 | 1 | ≤0.5 | 1 |
| *Candida albicans* NR-29368 | 2 | ≤0.5 | 4 | 2 | 2 | 8 | >64 |
| *Candida albicans* NR-29446 | 1 | ≤0.5 | 1 | 2 | 2 | 8 | >64 |
| *Candida albicans* ATCC MYA 573 | 1 | ≤0.5 | 1 | 2 | 2 | 16 | >64 |
| *Candida albicans* ATCC 64124 | 2 | ≤0.5 | 2 | 2 | 2 | 64 | >64 |
| *Candida krusei* ATCC 14243 | 32 | 4 | 32 | 64 | 32 | >64 | 64 |
| *Candida krusei* ATCC 34135 | 16 | 2 | 16 | 32 | 8 | >64 | 64 |
| *Candida parapsilosis* ATCC 22019 | 2 | 4 | 8 | 4 | 1 | ≤0.5 | 1 |
| *Candida glabrata* ATCC MYA-2950 | 8 | 16 | 8 | 8 | ≤0.5 | ≤0.5 | >64 |
| *Candida glabrata* ATCC 66032 | 8 | 16 | 8 | 4 | 1 | 1 | >64 |
| *Candida tropicalis* ATCC 1369 | 16 | 16 | 8 | 2 | 2 | 1 | >64 |
| *Candida tropicalis* ATCC 13803 | 4 | 4 | 8 | 4 | 1 | ≤0.5 | >64 |

FIGURE 6

Table 3.

| Strain Name | Compound/Drug Name | | | | | | |
|---|---|---|---|---|---|---|---|
| | 2 | 22 | 23 | 25 | 26 | 32 | Fluconazole |
| *Cryptococcus gattii* NR-43208 | ≤ 0.5 | ≤ 0.5 | ≤ 0.5 | ≤ 0.5 | ≤ 0.5 | ≤ 0.5 | 8 |
| *Cryptococcus gattii* NR-43209 | ≤ 0.5 | ≤ 0.5 | 1 | ≤ 0.5 | ≤ 0.5 | ≤ 0.5 | 8 |
| *Cryptococcus neoformans* NR-41292 | ≤ 0.5 | ≤ 0.5 | 1 | ≤ 0.5 | ≤ 0.5 | ≤ 0.5 | 8 |
| *Aspergillus brasiliensis* ATCC 16404 | > 64 | 4 | 32 | 64 | 32 | > 64 | >64 |
| *Aspergillus niger* ATCC 6275 | > 64 | 8 | 16 | > 64 | 32 | > 64 | >64 |
| *Aspergillus niger* ATCC 16888 | > 64 | 8 | 8 | > 64 | 16 | > 64 | >64 |
| *Aspergillus fumigatus* NR-35302 | 32 | 32 | > 64 | 64 | 16 | > 64 | >64 |
| *Aspergillus fumigatus* NR-35301 | 64 | 32 | > 64 | 64 | 16 | > 64 | >64 |

FIGURE 7

ARYL ISONITRILE COMPOUNDS AS A NEW CLASS OF POTENT, BROAD-SPECTRUM ANTIFUNGAL COMPOUNDS

CROSS REFERENCE

This application is a continuation in part for U.S. application Ser. No. 15/090,619, filed on Apr. 4, 2016, which claims the benefits of U.S. provisional application 62/143,031, filed on Apr. 4, 2015, under 35 § USC 119 (e). The contents of which are expressly incorporated entirely herein.

This application is directed generally to new antimicrobial compounds and more specifically, to aryl isonitrile compounds as a new class of potent broad-spectrum antifungal compounds, and their uses in treating drug resistant microbes.

GOVERNMENT RIGHT

This invention was made with government support under CA023168 awarded by National Institute of Health (NIH). The government has certain rights in the invention.

BACKGROUND

Invasive fungal infections caused by species of *Candida*, *Cryptococcus*, and *Aspergillus* afflict more than 1.5 million humans globally each year with a staggering mortality rate that often exceeds 50%.[1] *Candida* is the most frequent source of fungal infections worldwide; notably, *Candida albicans* is the fourth-leading cause of bloodstream infections, and is particularly problematic in immunocompromised patients.[2] There has been a global increase in the prevalence of invasive *Candida* infections in part due to the emergence of non-*albicans Candida* species including *Candida glabrata*, *Candida tropicalis*, *Candida parapsilosis*, and *Candida krusei*.[3, 4] In addition to *Candida*, species of *Cryptococcus* (including *C. neoformans* and *C. gatti*) are responsible for more than one million new invasive fungal infections each year that result in an astounding 625,000 deaths.[5] Patients co-infected with HIV are susceptible to severe cryptococcal infections that manifest primarily as pneumonia or meningoencephalitis.[6] The third fungal pathogen of concern involves species of *Aspergillus* (namely *A. fumigatus*) which are responsible for more than 300,000 fungal infections each year.[7] Invasive disease (particularly pulmonary infections) caused by *Aspergillus* primarily occur in patients with underlying conditions such as AIDS, cancer, cystic fibrosis, asthma, or individuals undergoing solid organ transplants. The severity of such infections can be seen by the low rate of survival (59%) reported for solid organ transplant recipients afflicted with invasive aspergillosis.[8]

The difficulty in treating invasive fungal infections has been exacerbated by the limited number of approved antifungal drugs. Currently, only three structurally-distinct classes of antifungal drugs are primarily used for treatment of invasive fungal infections—azoles (such as fluconazole), polyenes (such as amphotericin B), and echinocandins (such as caspofungin).[9] All three classes exert their antifungal activity by interfering with synthesis of a key component of the fungal cell membrane (ergosterol synthesis by both azoles and polyenes) or cell wall (β(1,3)-d-glucan synthesis by echinocandins).[9] Azole antifungals, including fluconazole, are considered the drugs of choice given their high oral bioavailability and reduced toxicity to host tissues. However, the clinical utility of fluconazole and other antifungal drugs has become increasingly limited due to the emergence of clinical isolates exhibiting resistance to these agents.[10, 11] This necessitates the development of new therapeutic agents. However, only one new antifungal drug class has been successfully developed in the past 30 years.[12] The development of new antifungal agents is very challenging given fungi and mammals are both eukaryotes; thus many proteins that are potential targets for antifungal therapy are also found in human cells, opening the door for potential toxicity concerns.[12, 13] There remains a need to identify antifungal compounds that are not toxic to human cells.

SUMMARY

The present study provides a set of aryl isonitrile compounds that possess broad-spectrum antifungal activity primarily against species of *Candida* and *Cryptococcus*. The most potent derivatives are capable of inhibiting growth of these key pathogens at concentrations as low as 0.5 µM. Remarkably, the most active compounds exhibit an excellent safety profile and are non-toxic to mammalian cells even at concentrations up to 256 µM.

Structures of

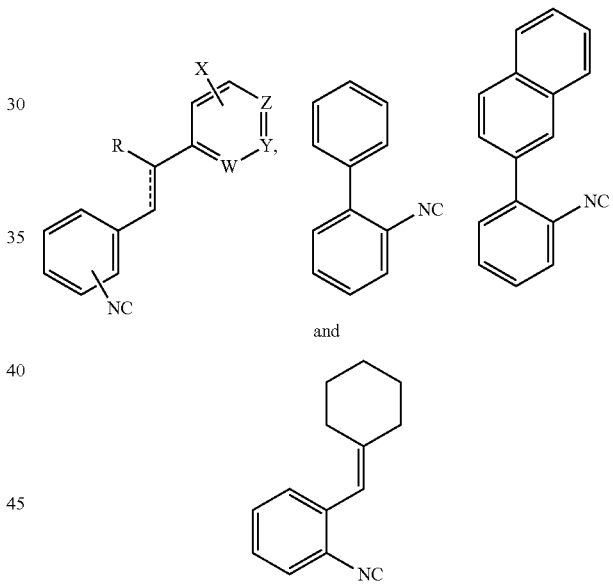

and are showing broad spectrum of antifungal activity without causing human cell toxicity.

Particularly, Compounds 2, 10, 19, 22, 23, 25, 26, 30, 32 in this disclosure are considered potent antifungal agent for further clinical applications.

In some embodiment, the above identified compounds may be used for treating both drug resistant bacterial infection and drug resistant fungal infection.

BRIEF DESCRIPTION OF DRAWINGS

FIG. 5 is Table 1 showing the minimum inhibitory concentration (MIC in µM) and minimum fungicidal concentration (MFC in µM) of synthesized compounds and fluconazole screened against C. albicans NR-29448.

FIG. 6 is Table 2 showing the minimum inhibitory concentration (MIC in µM) of synthesized compounds and fluconazole screened against clinical isolates of Candida albicans and non-albicans Candida species.

FIG. 7 is Table 3 showing the minimum inhibitory concentration (MIC in µM) of synthesized compounds and fluconazole screened against clinical isolates of Cryptococcus and Aspergillus.

DETAILED DESCRIPTION

While the concepts of the present disclosure are illustrated and described in detail in the figures and the description herein, results in the figures and their description are to be considered as exemplary and not restrictive in character. It is understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Given the dearth of antifungal drug classes and the emergence of resistance to key antifungal drugs (such as fluconazole), there is a need for new chemical scaffolds and compounds exhibiting potent, broad-spectrum antifungal activity and low toxicity to host (mammalian) tissues.

Figure 2:
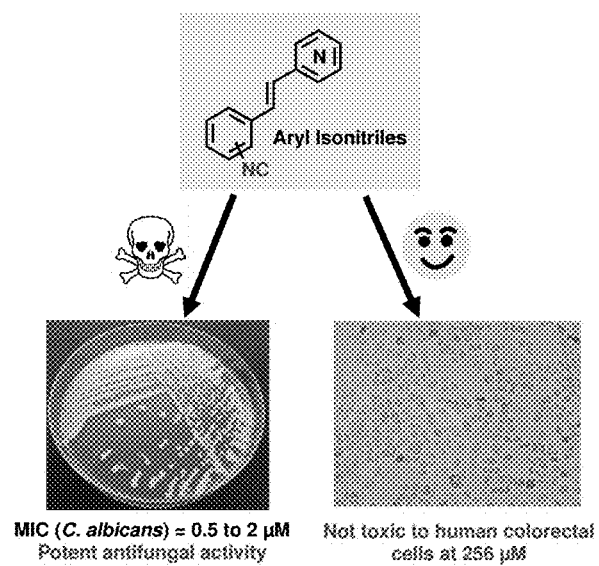
FIG. 2 A graphical abstract of current study.

Ideally, a novel therapeutic agent for invasive fungal infections should possess broad-spectrum antifungal activity with limited toxicity to host (human) tissues. In the search for new antimicrobial drug scaffolds, we recently discovered synthetic aryl isonitrile compounds that exhibit notable antibacterial activity against drug-resistant Staphylococcus aureus.[14] In addition, there are reports that natural product compounds containing the isonitrile functional group can possess dual antibacterial and antifungal activity, particularly against C. albicans. Per this observation, the present study investigates the structure-activity relationship of our synthetic aryl isonitrile compounds (FIG. 2) as antifungal agents, examines their spectrum of activity against pertinent species of Candida, Cryptococcus, and Aspergillus, and evaluates the most promising compounds' toxicity against mammalian cells. The synthesis scheme of various isonitrile analogue compounds can be found in the application Ser. No. 15/090,619 and are expressly incorporated herein.

The present disclosure shows aryl isonitrile compounds as a new scaffold for the development of antifungal agents. Structure-activity relationship studies reveal the presence of the isonitrile group and the inclusion of a second aromatic functional group are important for the compounds to possess potent antifungal activity. Compounds bearing the aryl isonitrile functional group exhibited broad-spectrum activity in inhibiting growth of notable species of Candida and Cryptococcus at a concentration as low as 0.5 µM. The compounds appear to be fungistatic against C. albicans. The most active compounds exhibit an excellent safety profile, as they are non-toxic to mammalian cells, even at concentrations up to 256 µM. The SAR information presented in this report will prove critical for the medicinal chemistry community to develop new aryl isonitrile analogues to advance them to the next step in the antifungal drug discovery process.

Materials and Methods

1. Synthesis of Compounds

Synthetic schemes, and spectral data of all compounds, in addition to all intermediates, have been previously described by Davis D C, Mohammad H, Kyei-Baffour K, et al. Discovery and characterization of aryl isonitriles as a new class of compounds versus methicillin- and vancomycin-resistant Staphylococcus aureus. Eur. J. Med. Chem. 2015; 101: 384-390.

2. Fungal Strains and Reagents Used in this Study

Clinical isolates of Candida, Cryptococcus, and Aspergillus were obtained from the American Type Cell Culture (ATCC, Manassas, Va., USA) and BEI Resources (Manassas, Va., USA). HRT-18 cells were purchased from the American Type Culture Collection. Fluconazole was purchased commercially and dissolved in dimethyl sulfoxide (DMSO) to prepare a stock solution (10 mM). Yeast extract peptone dextrose (YPD), RPMI-1640 for MIC determination, 3-(N-Morpholino) propanesulfonic acid, 4-Morpholinepropanesulfonic acid (MOPS), phosphate-buffered saline (PBS), RPMI-1640 medium for cell culture assay, fetal horse serum, and 96-well plates were all purchased from commercial vendors.

3. Determination of Minimum Inhibitory Concentration (MIC) and Minimum Fungicidal Concentration (MFC)

The broth dilution assay, following the guidelines of the Clinical and Laboratory Standards Institute for yeasts (M27-A3)[19] and molds (M38-A2)[20], was utilized to determine the MIC of compounds and fluconazole against species of Candida, Cryptococcus, and Aspergillus using 96-well plates. Plates containing fungi and test agents were incubated at 37° C. for at least 44 hours for Candida spp. and Aspergillus spp. or 68 hours for Cryptococcus spp. before the MIC was determined by visual inspection. For determination of the minimum fungicidal concentration (MFC) against C. albicans NR-29448, aliquots (5 µL) were transferred from wells with no growth onto yeast extract peptone dextrose (YPD) agar plates. Plates were incubated at 37° C. for 18 hours before MFC (>99.9% decrease in colony-forming units) was recorded.

4. Time-Kill Assay Against C. albicans

C. albicans NR-29351 cells ($OD_{600}=0.524$) were diluted to $2.08\times10^5$ colony-forming units (CFU/mL) and exposed to concentrations equivalent to 4×MIC (in triplicate) of compounds 30, 32, and fluconazole in YPD medium. Aliquots (100 µL) were collected from each treatment after 0, 2, 4, 6, 8, 10, 12, and 24 hours of incubation at 37° C. and subsequently serially diluted in PBS. Fungi were then spotted onto YPD agar plates and incubated at 37° C. for at least 20 hours before viable CFU/mL was determined.

5. Cytotoxicity Analysis of Aryl Isonitrile Compounds

Compounds were assayed (at concentrations of 32, 64, 128, and 256 μM) against a human colorectal (HRT-18) cell line to determine the potential toxic effect to mammalian cells in vitro. Briefly, cells were cultured in RPMI-1640 medium supplemented with 10% fetal horse serum at 37° C. with $CO_2$ (5%). Control cells received DMSO alone at a concentration equal to that in drug-treated cell samples. The cells were incubated with the compounds (in triplicate) in a 96-well plate at 37° C. with $CO_2$ (5%) for two hours. The assay reagent MTS 3-(4,5-dimethylthiazol-2-yl)-5-(3-carboxymethoxyphenyl)-2-(4-sulfophenyl)-2H-tetrazolium) (Promega, Madison, Wis., USA) was subsequently added and the plate was incubated for four hours. Absorbance readings (at $OD_{490}$) were taken using a kinetic microplate reader (Molecular Devices, Sunnyvale, Calif., USA). The quantity of viable cells after treatment with each compound was expressed as a percentage of the viability of DMSO-treated control cells (average of triplicate wells±standard deviation). The toxicity data was analyzed via a two-way ANOVA, with post hoc Dunnet's multiple comparisons test (P<0.05), utilizing GraphPad Prism 6.0 (GraphPad Software, La Jolla, Calif.).

Examples

1 Structure-Activity Relationship of Compounds Against *Candida albicans*

In this Example, we demonstrated that the presence of the isonitrile group provides compounds antifungal activity and the antifungal mode of action appears to be different from antimicrobial action.

Figure 1:
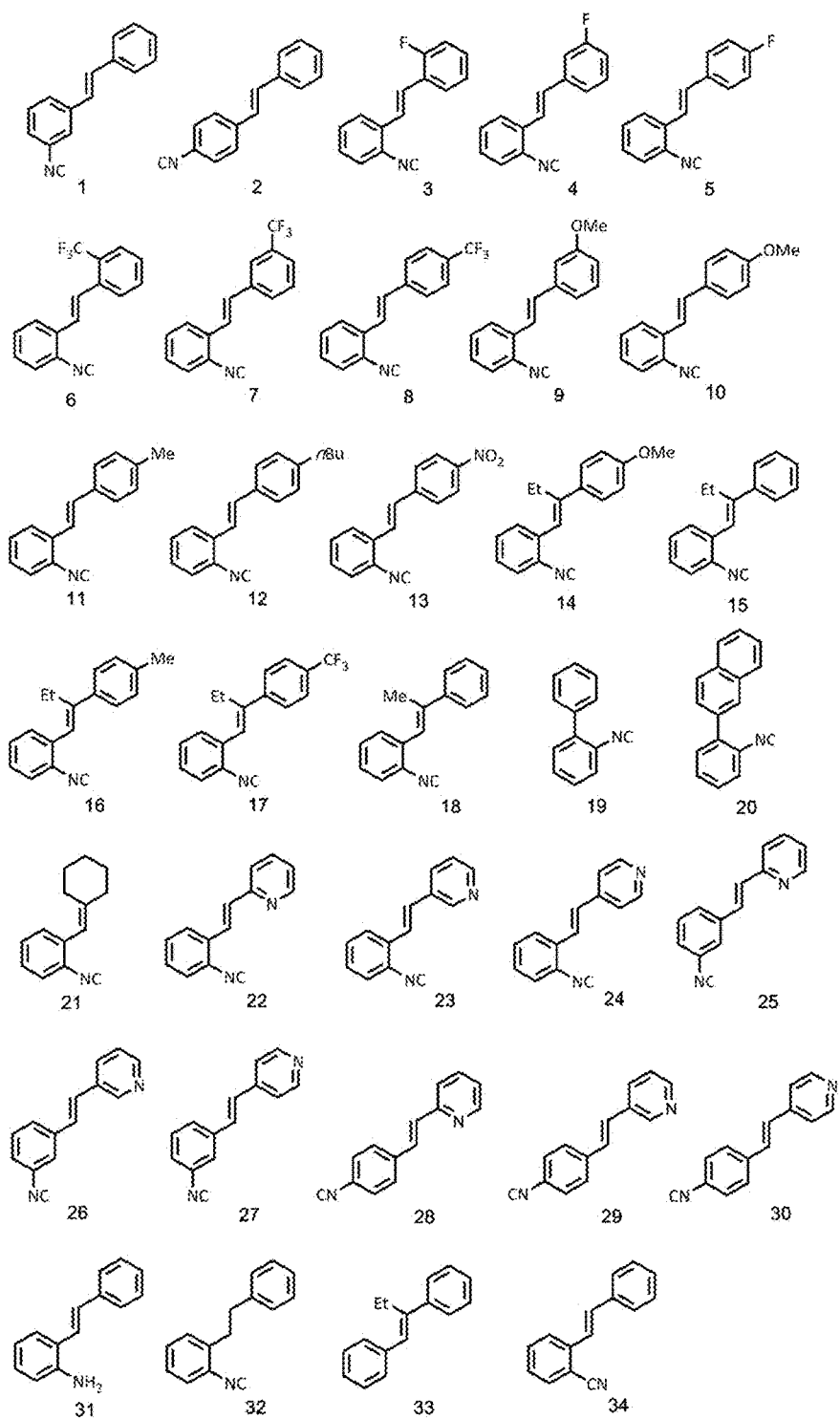
FIG. 1 Chemical structures of compounds presented in this study.

As noted by Beck-Sague et al., *Candida albicans* has been identified as the most common fungal pathogen isolated from healthcare-associated infections in humans.[17] Thus we initially evaluated our collection of compounds (list of compounds in FIG. 1) for antifungal activity against a clinical isolate of *C. albicans* (see Table 1). Using the broth microdilution assay, the minimum inhibitory concentration (MIC) was determined. The initial screening provided key insight into the structure-antifungal activity relationship of the compounds. Most notably, the presence of the isonitrile group appears to be critical for the compounds to possess antifungal activity. Compounds lacking the isonitrile group (as in 33) or where the isonitrile was substituted with alternative groups including an isosteric nitrile group (34) or an amine (31) were inactive (MIC≥64 μM).

For the stilbene-backbone isonitriles, most of them showed promising antifungal activity against *C. albicans* (MIC= or <8 μM) with a few exceptions (cf. 5, 6, 8, 9, 14, 15, 17, MIC= or >16 μM). The effect of different substituents on the aromatic ring without the isonitrile group varies. Both electron-donating (cf. OMe, Me, nBu) and electron-withdrawing (F, $CF_3$, $NO_2$) groups can be tolerated to a certain extent based on the positions of the substituents. In general, adding alkyl substituents (Me or Et) on the trans double bond decreased the antifungal activity. For example, compound 10 (MIC=1 μM) is much more potent than compound 14 with an extra ethyl group on the double bond (MIC=64 μM); compound 11 (MIC=2 μM) and compound 8 (MIC=32 μM) are two-fold more potent than compound 16 (MIC=4 μM) and compound 17 (MIC>64 μM), respectively. The para-$CF_3$ group of compounds 8 and 17 has a dramatic effect on their antifungal activity and both compounds 8 and 17 are significantly less potent (16-fold higher in MIC value) than the corresponding para-$CH_3$ substituted analogs. The possession of the stilbene backbone is not necessary for the aryl isonitriles' antifungal activity against *C. albicans* though it does enhance potency in several cases. For example, replacing the second aromatic group with a cyclohexane (21) resulted in a compound with good antifungal activity against *C. albicans* (MIC=4 μM). The biaryl isonitriles 19 and 20 are potent antifungal compounds against *C. albicans* with 0.5 μM and 2 μM MIC values respectively and the naphthyl group decreased the potency about 4-fold. Interestingly, in our previous studies,[14] both 19 and 20 only showed weak or even no antimicrobial activity against methicillin-resistant *Staphylococcus aureus* (MRSA) strains. Compound 32 with a saturated two-carbon linker between the two aryl groups showed potent anti *C. albicans* activity as well (MIC=0.5 μM). Again, compound 32 was not a good candidate against several MRSA strains in our previous studies. These observations suggest that the antifungal and antibacterial modes of actions for these isonitrile compounds are very likely to be different.

Replacing the non-isonitrile-bearing aromatic ring with pyridine showed beneficial effect on the antifungal activity against *C. albicans*. For example, the MIC values of isomeric compounds 22 to 30 range from 0.5 μM to 4 μM, with compound 25 emerging as the most potent analogue. The effect of the positions of the isonitrile group on the aromatic ring as well as the nitrogen atom of the pyridine ring ranges from two- to eight-fold, which are quite significant. When the isonitrile group is ortho to the double bond (22, 23, 24), the 2 and 3-pyridyl substituted compounds 22 and 23 (MIC=1 μM) are four times more potent than the 4-pyridyl substituted compound 24 (MIC=4 μM). When the isonitrile group is meta to the double bond (25, 26, 27), the 2-pyridyl substituted compound 25 (MIC=0.5 μM) is four- or eight-fold more active than the 3 or 4-pyridyl substituted 26 (MIC=2 μM) or 27 (MIC=4 μM), respectively. When the isonitrile group is para to the double bond (28, 29, 30), the effect of the position of the pyridine nitrogen is quite small and 4-pyridyl substituted 30 (MIC=1 μM) is two-fold more active than the 2 and 3-pyridyl substituted one.

Overall, the structure-activity analysis revealed three key findings: the presence of the aryl isonitrile functional group is essential for the observed antifungal activity, the addition of a second aromatic functional group enhances the antifungal activity of the compounds, and the positioning of the isonitrile group on the aromatic ring also impacts the biological activity of the compounds. Interestingly, analogues exhibiting the most potent antifungal activity (including 7, 11, 19, 20, and 32) possessed only modest or weak antibacterial activity against drug-resistant *S. aureus*.[14] This information is critical to help guide the synthesis of future aryl isonitrile analogues to improve their specificity as antifungal agents.

2. Aryl Isonitrile Compounds Exhibit Fungistatic Behavior Against *C. albicans*

This Example shows certain identified isonitrile compounds are fungistatic.

After discovering the aryl isonitrile compounds are potent inhibitors of *C. albicans* growth, we were curious to evaluate whether the compounds simply inhibit fungal growth (are fungistatic) or are capable of killing the microorganism (are fungicidal). Previously, we determined that the aryl isonitrile compounds are bacteriostatic, thus we postulated that the compounds would be fungistatic. To investigate this point, the minimum fungicidal concentration (MFC) required to reduce the number of colony-forming units (CFU) by 99.9%,[18] was determined for the active compounds against *C. albicans* NR-29351. The MFC values for the active compounds were found to be noticeably higher (more than 8-fold) compared to their MIC results (Table 1), supporting the notion that the compounds are fungistatic. These results aligned with the results obtained with fluconazole, an antifungal drug known to exhibit fungistatic activity against *C. albicans*.[18]

Figure 3:
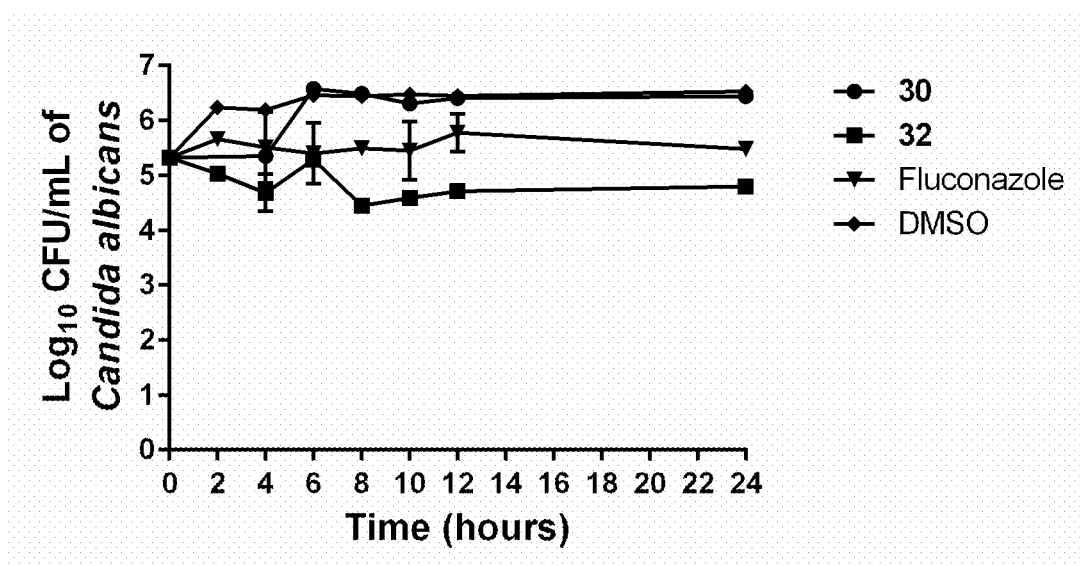
FIG. 3 Time-kill analysis of aryl isonitrile compounds 30, 32, and fluconazole against *Candida albicans* NR-29351 over a 24 hour incubation period at 37° C. DMSO served as a negative control. The error bars represent standard deviation values obtained from triplicate samples used for each compound/antifungal drug studied.

In order to verify this observation, two of the most potent antifungal compounds were subjected to a traditional time-kill assay. Even at a high concentration (4×MIC), the aryl isonitrile compounds exhibited fungistatic behavior against *C. albicans* (FIG. 3). Neither 30 nor 32 produced a 3-$\log_{10}$ reduction in fungal CFU within 24 hours, which would be characteristic of fungicidal activity. The compounds' behavior matches that observed with fluconazole. Thus preliminary inspection indicates the aryl isonitrile compounds are fungistatic agents (particularly against *C. albicans*).

3. Aryl Isonitrile Compounds Exhibit Broad-Spectrum Antifungal Activity

In this Example, we demonstrated that several aryl isonitrile compounds possess broad-spectrum antifungal activity to clinical relevant strains.

Given the potent antifungal activity observed with several aryl isonitrile compounds against *C. albicans*, we next moved to assess their spectrum of activity against key pathogenic fungi. Interestingly, several current antifungal drugs suffer from their inability to inhibit growth of multiple species of fungi. For example, azole antifungals such as fluconazole are generally very effective at inhibiting growth of yeasts such *Candida albicans* and species of *Cryptococcus*; however, fluconazole is ineffective at inhibiting growth of molds such as *Aspergillus* species.[12] Even more discouraging, non-*albicans Candida* species including *Candida glabrata* and *Candida krusei* are intrinsically resistant or less susceptible to fluconazole.[12] In contrast, echinocandins are effective against *Candida* and *Aspergillus* but are ineffective as treatment options for infections caused by *Cryptococcus*.[12] Thus finding antifungal compounds capable of inhibiting growth of species of *Candida, Cryptococcus*, and *Aspergillus* is highly desirable.

Based upon their potent inhibitory effect against *C. albicans*, six aryl isonitrile compounds (2, 22, 23, 25, 26, and 32) were screened against 21 additional clinical isolates including non-*albicans Candida* species such as *Candida glabrata, Candida tropicalis, Candida parapsilosis, Candida krusei* (Table 2) in addition to species of *Cryptococcus* and *Aspergillus* (Table 3). Interestingly, all seven compounds were able to inhibit growth of all species of the yeasts *Candida* and *Cryptococcus*. In general, compound 32 proved the most potent compound as it inhibited growth of all clinical isolates, with the exception of *C. krusei*, with a MIC ranging from 0.5 to 1 µM (Table 2). This proved to be more potent than fluconazole (MIC=2 µM) against strains of *C. albicans* and *Cryptococcus gattii* that are sensitive to this drug. Against fluconazole-resistant strains of *Candida albicans*, compounds where the second aromatic substituent was replaced with a pyridine were generally more active than 32. For example, compounds 22, 23, 25, and 26 had MIC values that were lower than compound 32 against fluconazole-resistant *C. albicans*. However, against non-*albicans Candida* species, compounds containing the pyridine functional group, with the exception of 26, had MIC values that were two to 32-fold higher than the analogue containing a second aromatic group (32).

Though the six aryl isonitrile compounds exhibited potent antifungal activity against yeasts (*Candida* and *Cryptococcus*), they were less active against molds. Against *Aspergillus fumigatus*, the MIC values were equal to or higher than 16 µM for all six compounds (Table 3). Compound 22 exhibited the most potent activity against both *A. niger* and *A. brasiliensis* with MIC values ranging from 4 to 8 µM. This was a marked improvement over fluconazole, which proved ineffective at inhibiting growth of both *A. niger* and *A. brasiliensis* (MIC>64 µM).

4 Compounds are not Toxic to Mammalian Cells at High Concentrations

In this Example, we demonstrated that herein identified antifungal aryl isonitrile compounds are not toxic to mammalian cells, therefore paving the way for future development of these as antifungal drugs.

Toxicity is a fundamental parameter to evaluate in early-stage drug discovery to ensure compounds with promising biological activity do not also possess harmful effects to host (human) tissues. A significant challenge with several currently approved antifungal drugs is toxicity. Amphotericin B is a broad-spectrum, fungicidal agent effective against *Candida, Cryptococcus*, and *Aspergillus*. However, one of amphotericin B's (and polyenes in general) most significant limitations is its severe toxicity to host tissues.[12] Though a lipid formulation of amphotericin B has been developed that exhibits less toxicity, the formulation is too expensive to be administered in resource-limited regions where invasive fungal infections are endemic.[12] Thus identifying antifungal agents with broad-spectrum activity and limited toxicity to host tissues is highly desirable.

Figure 4:
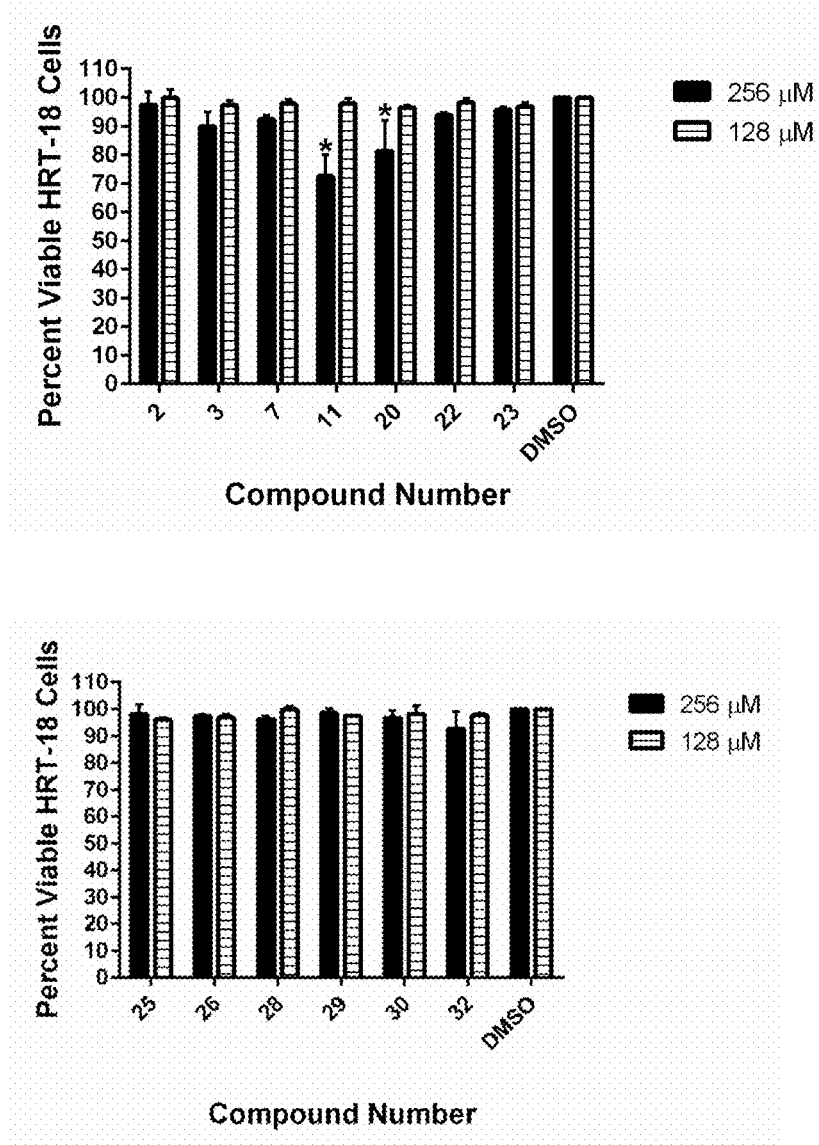
FIG. 4 Toxicity analysis of aryl isonitrile compounds against human epithelial colorectal cells (HRT-18). Percent viable mammalian cells (measured as average absorbance ratio (test agent relative to DMSO)) for cytotoxicity analysis of compounds (tested in triplicate) at 128 and 256 µM against HRT-18 cells using the MTS assay. Dimethyl sulfoxide (DMSO) served as a negative control to determine a baseline measurement for the cytotoxic impact of each compound. The absorbance values represent an average of a minimum of three samples analyzed for each compound. Error bars represent standard deviation values for the absorbance values. A two-way ANOVA, with post hoc Dunnet's multiple comparisons test, determined no statistical difference between the values obtained for each compound and DMSO ($P<0.05$).

Previously, we evaluated the toxicity of the aryl isonitrile compounds against murine macrophage cells and found the most potent analogues were not toxic up to a concentration of 64 µM.[14] To further examine the toxicity profile of the aryl isonitrile compounds, the MTS assay was utilized to evaluate the compounds' toxicity against a human epithelial colorectal (HRT-18) cell line at very high concentrations (up to 256 µM). As presented in FIG. 4, no compound was toxic to HRT-18 cells at a concentration of 128 µM. Astonishingly, even at a concentration of 256 µM, all compounds were non-toxic with the exception of 11 and 20. This represents a nearly 512-fold difference between the MIC of the most potent compounds against fungi (such as 26 and 32) and the highest concentration where no toxicity was observed to mammalian cells. This result supports our previous findings that the aryl isonitrile compounds have an excellent safety profile against mammalian cells that warrants further evaluation. The lack of toxicity observed against mammalian cells suggests the aryl isonitrile compounds may exert their antifungal effect via a unique mechanism.

REFERENCES

1. Brown G D, Denning D W, Gow N A R, et al. Hidden Killers: Human Fungal Infections. *Sci Transl Med.* 2012; 4.
2. Wisplinghoff H, Bischoff T, Tallent S M, et al. Nosocomial bloodstream infections in US hospitals: analysis of 24,179 cases from a prospective nationwide surveillance study. *Clin Infect Dis.* 2004; 39: 309-317.
3. Pfaller M A. Antifungal drug resistance: mechanisms, epidemiology, and consequences for treatment. *Am. J. Med.* 2012; 125(1 Suppl): S3-13.
4. Sardi J C, Scorzoni L, Bernardi T, et al. *Candida* species: current epidemiology, pathogenicity, biofilm formation, natural antifungal products and new therapeutic options. *J. Med. Microbiol.* 2013; 62(Pt 1): 10-24.
5. Park B J, Wannemuehler K A, Marston B J, et al. Estimation of the current global burden of cryptococcal meningitis among persons living with HIV/AIDS. *Aids.* 2009; 23: 525-530.

6. Butts A, Koselny K, Chabrier-Rosello Y, et al. Estrogen Receptor Antagonists Are Anti-Cryptococcal Agents That Directly Bind EF Hand Proteins and Synergize with Fluconazole In Vivo. *Mbio.* 2014; 5:1-11.
7. The Fungal Infection Trust. How common are fungal diseases? Updated September 2016. URL: http://www-.fungalinfectiontrust.org/wp-content/uploads/2015/12/How-Common-are-Fungal-Diseases5.pdf
8. Pappas P G, Alexander B D, Andes D R, et al. Invasive Fungal Infections among Organ Transplant Recipients: Results of the Transplant-Associated Infection Surveillance Network (TRANSNET). *Clin Infect Dis.* 2010; 50: 1101-1111.
9. Koselny K, Green J, DiDone L, et al. The Celecoxib Derivative AR-12 Has Broad-Spectrum Antifungal Activity In Vitro and Improves the Activity of Fluconazole in a Murine Model of Cryptococcosis. *Antimicrob. Agents Chemother.* 2016; 60: 7115-7127.
10. Kanafani Z A, Perfect J R. Antimicrobial resistance: resistance to antifungal agents: mechanisms and clinical impact. *Clin Infect Dis.* 2008; 46: 120-128.
11. Ben-Ami R, Garcia-Effron G, Lewis R E, et al. Fitness and virulence costs of *Candida albicans* FKS1 hot spot mutations associated with echinocandin resistance. *J Infect Dis.* 2011; 204: 626-635.
12. Roemer T, Krysan D J. Antifungal drug development: challenges, unmet clinical needs, and new approaches. *Cold Spring Harbor Perspectives in Medicine.* 2014; 4.
13. Denning D W, Bromley M J. How to bolster the antifungal pipeline. *Science.* 2015; 347: 1414-1416.
14. Davis D C, Mohammad H, Kyei-Baffour K, et al. Discovery and characterization of aryl isonitriles as a new class of compounds versus methicillin- and vancomycin-resistant *Staphylococcus aureus*. *Eur. J. Med. Chem.* 2015; 101: 384-390.
15. Raveh A, Carmeli S. Antimicrobial ambiguines from the cyanobacterium *Fischerella* sp. collected in Israel. *J. Nat. Prod.* 2007; 70: 196-201.
16. Mo S Y, Krunic A, Chlipala G, Orjala J. Antimicrobial Ambiguine Isonitriles from the Cyanobacterium *Fischerella ambigua*. *J. Nat. Prod.* 2009; 72: 894-899.
17. Beck-Sague C, Jarvis W R. Secular trends in the epidemiology of nosocomial fungal infections in the United States, 1980-1990. National Nosocomial Infections Surveillance System. *J Infect Dis.* 1993; 167: 1247-1251.
18. Graybill J R, Burgess D S, Hardin T C. Key issues concerning fungistatic versus fungicidal drugs. *Eur J Clin Microbiol.* 1997; 16: 42-50.
19. Clinical and Laboratory Standards Institute. M27-A3, Reference Method for Broth Dilution Antifungal Susceptibility Testing of Yeasts; Approved Standard—Third Edition. Wayne, Pa.; 2008.
20. Clinical and Laboratory Standards Institute. M38-A2; Reference Method for Broth Dilution Antifungal Susceptibility Testing of Filamentous Fungi; Approved Standard Wayne, Pa.; 2008.

The invention claimed is:

1. A method of treating a fungus infection in a patient in need thereof, comprising administering to the patient a therapeutically effective amount of an aryl isonitrile compound having the structure of

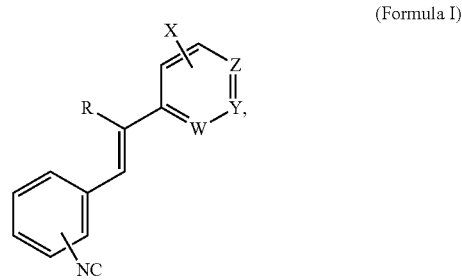

(Formula I)

wherein R is hydrogen or an alkyl, X is hydrogen, a halogen, an alkoxy, trihalomethyl, nitro, or an alkyl, W, Y and Z are each independently —CH or N wherein W, Y and Z are all —CH or only one of W, Y, and Z is N and the other of W, Y and Z are —CH, and pharmaceutically acceptable salts thereof.

2. The method of claim 1, wherein the amount of the isonitrile compound is from about 0.5 µM to about 256 µM.

3. The method of claim 1, wherein the species of fungus is selected from the group consisting of *Candida, Cryptococcus*, and *Aspergillus* and the combination thereof.

4. The method of claim 1, wherein R is hydrogen, X is selected from hydrogen, trihalomethyl, alkoxy and methyl, and W, Y and Z are —CH—.

5. The method of claim 1, wherein R and X are hydrogen.

6. The method of claim 1, wherein R and X are hydrogen, W and Y are —CH—, and Z is selected from —CH— and N.

* * * * *